United States Patent [19]
Steer

[11] Patent Number: 5,261,708
[45] Date of Patent: Nov. 16, 1993

[54] OSTOMY COUPLING

[75] Inventor: Peter L. Steer, Surrey, England

[73] Assignee: E. R. Squibb & Sons, Inc., Princeton, N.J.

[21] Appl. No.: 676,041

[22] Filed: Mar. 27, 1991

[51] Int. Cl.$^5$ .............................................. A61F 5/44
[52] U.S. Cl. ................................. 285/319; 285/921; 604/342; 604/338; 604/339
[58] Field of Search ............... 604/338, 339, 332, 342; 285/319, 921

[56] References Cited

U.S. PATENT DOCUMENTS

| | | | |
|---|---|---|---|
| 3,528,420 | 9/1970 | Nielsen | 604/342 |
| 4,419,100 | 12/1983 | Alexander | 604/339 |
| 4,460,363 | 7/1984 | Steer et al. | 604/339 |
| 4,610,676 | 9/1986 | Schneider et al. | 604/339 |
| 4,610,677 | 9/1986 | Mohiuddin | 604/339 |
| 4,775,373 | 10/1988 | Steer | 604/339 |
| 4,781,708 | 11/1988 | Steer | 604/338 |
| 4,846,798 | 7/1989 | Holtermann et al. | 604/339 |
| 4,872,869 | 10/1989 | Johns | 604/339 |
| 4,889,534 | 12/1989 | Mohiuddin et al. | 604/339 |
| 4,950,261 | 8/1990 | Steer | 604/339 |
| 4,973,324 | 11/1990 | Steer | 604/342 |
| 5,088,972 | 2/1992 | Edwards | 604/338 |
| 5,178,615 | 1/1993 | Steer et al. | 604/338 |

FOREIGN PATENT DOCUMENTS

| | | | |
|---|---|---|---|
| 2179556 | 3/1987 | United Kingdom | 604/342 |
| 2183481 | 6/1987 | United Kingdom | 604/342 |
| 2219507 | 12/1989 | United Kingdom | 604/339 |
| 9101118 | 2/1991 | United Kingdom | 604/342 |

Primary Examiner—Eric K. Nicholson
Attorney, Agent, or Firm—Stuart E. Krieger

[57] ABSTRACT

An ostomy coupling has first and second coupling elements. One has a flange carrying a wall upstanding therefrom, the free end of this wall having an inwardly or outwardly extending sealing and latching member. The other coupling element has an inner (second) annular wall surrounding a stomal orifice and, radially outwardly therefrom, a third annular wall. The second or the third annular wall carries a projection arranged to cooperate with the free end of the sealing and latching member. The inner or outer surface of the first annular wall as the case may be and a confronting surface of the second or the third annular wall are tapered in a complementary manner.

6 Claims, 4 Drawing Sheets

FIG. 3
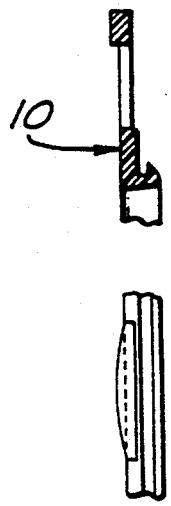
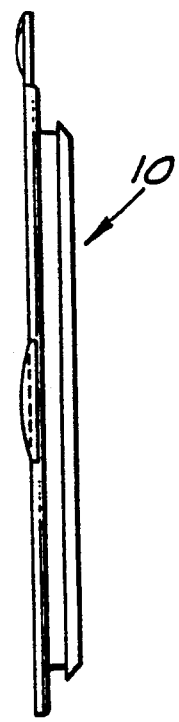
FIG. 5
FIG. 4
FIG. 6
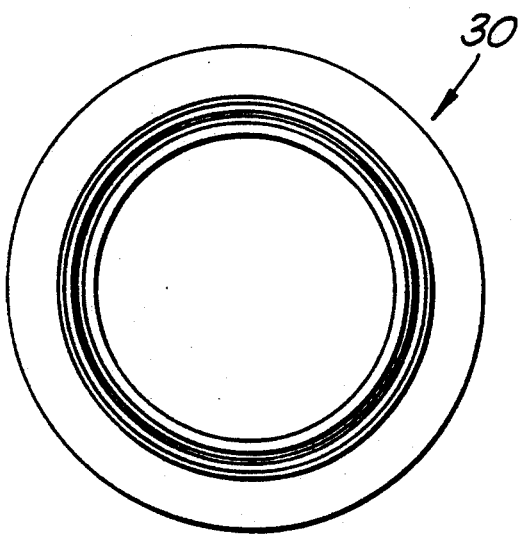
FIG. 7

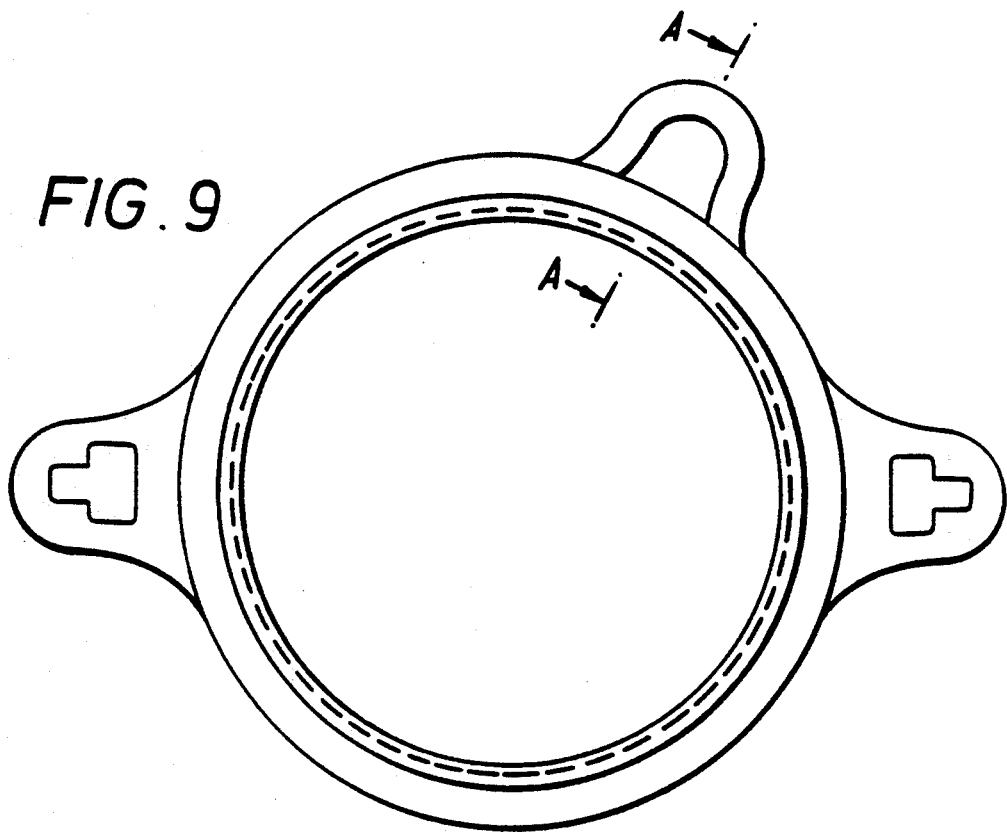
FIG. 9

OSTOMY COUPLING

This invention relates to an ostomy coupling.

There have been many attempts to devise ostomy couplings, and one particular design has been widely successful, see U.K. Patent No. 1 571 657. It would be desirable, however, if there existed a low profile system with a light fitting pressure and yet a high latch release pressure. By 'low profile' in this context is meant a coupling which stands out from the body of the wearer by only a small distance. This is desirable because wearers of ostomy appliances do not wish them to give rise to a bulge under clothing and, ideally, they should not be noticeable even under light sports clothing.

According to the present invention, there is provided an ostomy coupling comprising first and second coupling elements of which one has a flange carrying a first annular wall upstanding therefrom, the free end of this wall having a radially outwardly extending sealing and latching member, the other coupling element having an annular wall (herein called a second annular wall) surrounding a stomal orifice and, radially outwardly therefrom, a third annular wall of lesser height than the second annular wall and carrying an inwardly extending projection to cooperate with the sealing and latching member.

In accordance with one preferred embodiment of the invention, the inner surface of the first annular wall and the outer surface of the second annular wall are tapered in a complementary manner. For example these surfaces are preferably both shaped as a frustum of a cone with a cone angle of from 4 to 16 degrees, preferably 6-10 degrees, and desirably 10 degrees. In other words, the angle of the outer surface of the second annular wall to the axis of the coupling, measured in a radial plane, may be from 2 to 8 degrees, preferably 3 to 5 degrees and most preferably about 3 or 4 degrees. The main purposes of this taper are to achieve good sealing and to ensure the proper relative orientation between the tip of the sealing and latching member and its confronting projection on the third annular wall, when the elements are in their mutually coupled condition.

In use, due to the direction in which the sealing and latching member extends, coupling of the elements is achieved with only a small applied force since the tip of the latching and sealing member slides smoothly past a surface of the third annular wall. On the other hand, to uncouple, a greater pulling force must be applied in order to bend and deform the sealing and latching member so that it can be pulled past the projection. Best results have been achieved, from the point of view of securing a light fitting but high latch release pressure by providing the projection with a surface located at from 25 to 35, preferably about 30 degrees to the horizontal, assuming the coupling element to be located with the major surface of its flange horizontal.

In a preferred embodiment of the invention, the first coupling element is the bag-side coupling element and is advantageously attached to the wall of an ostomy bag, and the second coupling element is the body-side coupling element which in normal use is fixed to one side of a pad of medical grade adhesive having protective and curative properties. This pad may have a central stomal orifice or may have a central portion which can be removed to provide such an orifice. As is well known in ostomy couplings, such medical grade adhesive pads may have paper layers carrying a diagram to assist the user in cutting out the central portion to provide a stomal orifice, if a stomal orifice is not already present.

Also according to the present invention, there is provided an ostomy coupling comprising first and second coupling elements of which one has a flange carrying a first annular wall projecting therefrom, the free end of this wall having a radially inwardly extending sealing and latching member; the other coupling element having an annular radially inner second wall surrounding a stomal orifice and a radially outer third annular wall of lesser height than the second wall, the second wall carrying an outwardly extending projection to co-operate with the sealing and latching member.

It will be seen that this arrangement can be regarded as a 'mirror image' of the arrangement referred to in the third paragraph of this specification.

Illustrative examples of the present invention will be better understood from the following particular description given with reference to the drawings in which:

FIGS. 2, 3, 4 and 5 are respectively front view, scrap section on line A—A, side view, and scrap section on centre line through the belt tab, of one example of a first (bag-side) coupling element; and FIGS. 6 and 7 are respectively a front view and a side view of one example of a second (body-side) coupling element;

FIGS. 9, 10, 11 and 12 are respectively front view, scrap section on line A—A, side view, and scrap section on centre line through the belt tab of a first (bag-side) coupling element according to the second embodiment.

Figure 1:
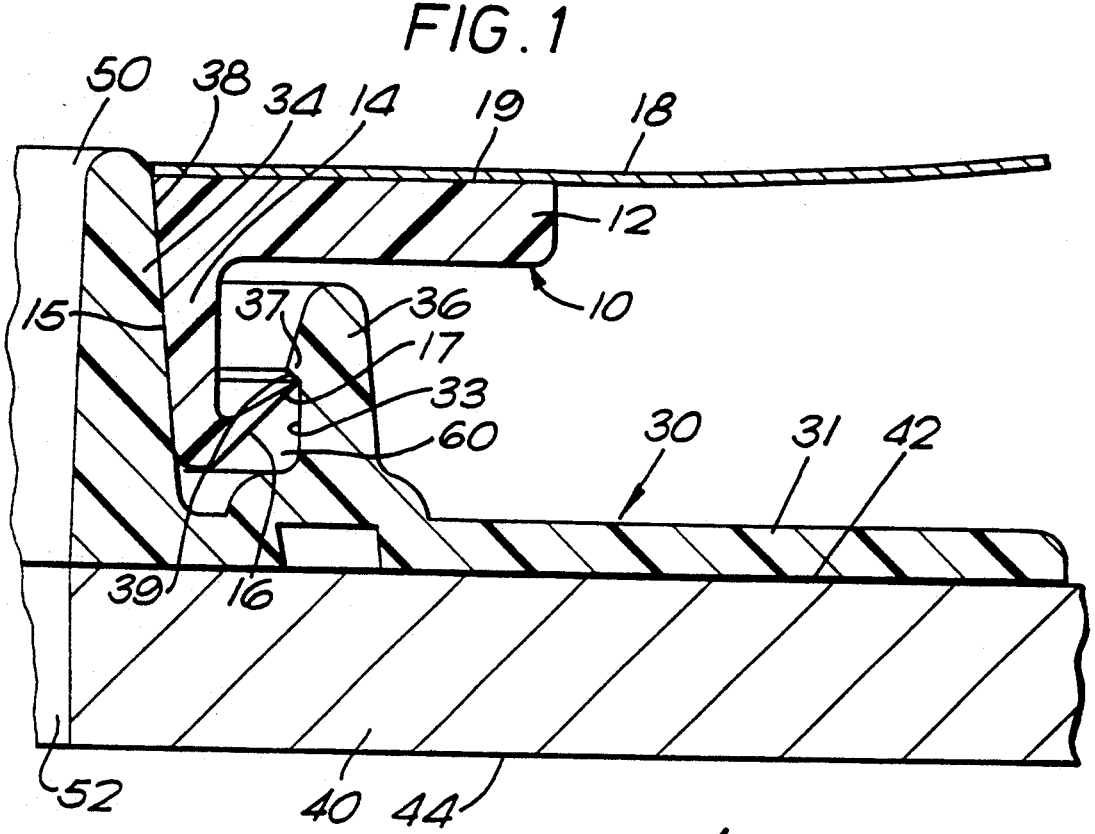
FIG. 1 is a cross-section in an axial plane, taken through the rotational axis of the coupling, showing half of one example of ostomy coupling according to the invention on a larger scale than used in FIGS. 2–7.
Figure 2:
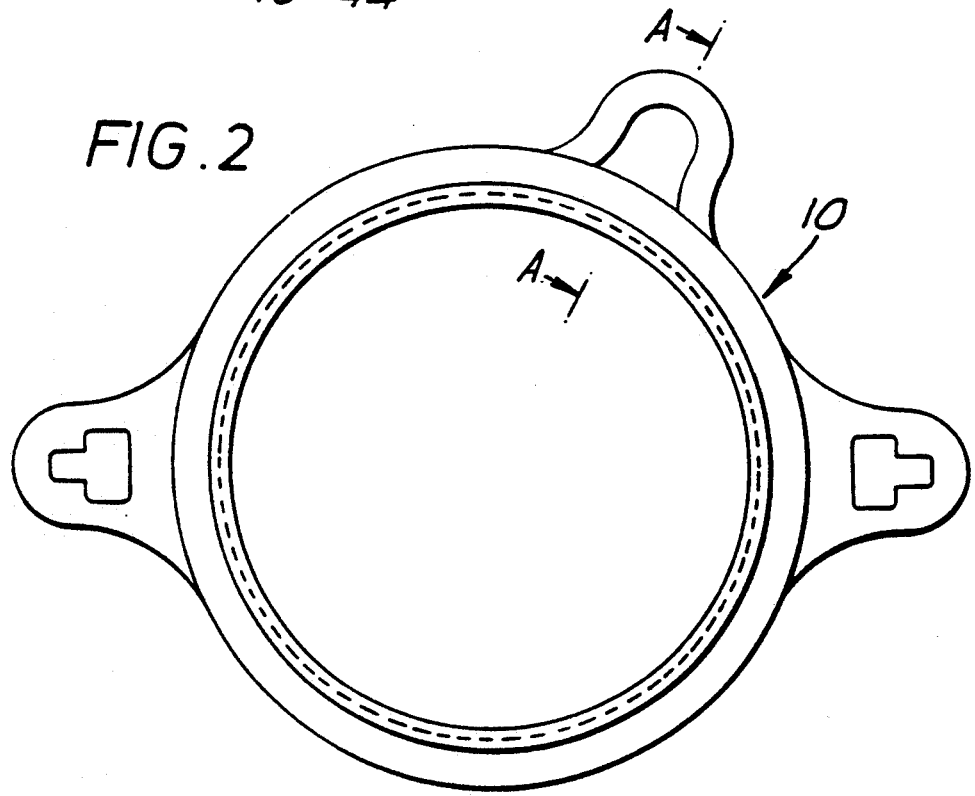

The particular embodiment of the invention illustrated in FIGS. 1–7 is a two-part coupling by which an ostomy bag or pouch can be connected to a pad by using a light fitting pressure, but which requires a relatively heavier separating force to detach a filled bag with its bag-side coupling element from the body-side coupling element which remains on the medical grade adhesive pad. Two-part ostomy couplings are already known, see for example British Patents Nos. 1 571 657 and 1 568 860. The present invention adopts a two-stage approach to satisfactory sealing between the two coupling elements, involving the cooperation of substantially conically tapered surfaces on the body-side and bag-side coupling elements and the cooperation of a resilient plastic latching and sealing member on one element with a confronting projecting surface of special shape upon the other coupling elements.

The illustrated bag-side coupling element 10 comprises a substantially circular flange 12 having a flat surface 19 over which an ostomy bag wall 18 is secured by welding, adhesive or in any other convenient manner. Integral with the flange 12 is a first annular wall 14 which has a tapered inner wall surface 15 and, at its end further from the flange 12, has an integral sealing and latching member 16. This member 16 extends around the entire periphery of the first coupling element. The element is preferably made of a synthetic plastics material, for example ethylene vinyl acetate polymer. That known by the grade number UL00209 and available from Esso Petroleum Company Limited is an example of a suitable material. Of course other materials may be used.

A second body-side coupling element 30 includes a generally circular flange 31 surrounding a stomal orifice 50 and having a surface which may be joined a pad 40 of a medical grade adhesive by, for example, an adhesive layer 42. The second coupling element may be joined to the medical grade adhesive pad by other means if desired. The medical grade adhesive pad has a surface 44 which is intended for direct application to the peristomal area of the skin of the wearer. Suitable material for the pad 40 is that known as "Stomahesive" (Registered Trademark) or that known as "Duoderm" (Trademark) available from ConvaTec Limited, Ickenham, Middlesex. Other suitable medical grade adhesive materials are available and may be employed instead. There is a stomal orifice 52 in the pad 40. Alternatively, the pad may carry a label marking the area of the centre of the pad which is to be cut out in order to produce a suitable stomal orifice. In use the intending wearer cuts out a central generally circular portion before application of the pad to the peristomal skin area. The second coupling element 30 may advantageously be made of low density polyethylene, e.g. Esso Grade 600 BA, but other suitable materials are available and may be used instead.

The second coupling element includes a radially inner annular wall 34 and a radially outer annular wall 36. The wall 34 has a substantially conically tapered outer surface 38. A taper of this surface is arranged to be complementary to that of the surface 15 of the element 12. The height of the wall 34 is greater than the height of the wall 14 of the element 12. The shape of the inner wall surface of the wall 34 is not of critical importance except that it is desirable for it to be as smooth as possible so not offering any crevices or impediments to exit of discharged body wastes. These pass from the stoma of the wearer into the bag, one wall 18 of which only is shown.

The outer annular wall 36 is of lesser height than the wall 34 and its inner surface has a projection 37 which extends inwardly forming a "nose" at a precisely defined height. This projection 37 extends completely around the wall 36 and is bounded on its lower side as seen in the drawing by an angled annular surface 39. The position of this projection and the position of the sealing and latching member 16 and the dimensions of the first and second coupling elements are chosen so that in the normal mutually coupled position of the two parts the tip of the sealing and latching member 16 takes up a position in contact with the angled join between the surface 39 and the lower part 33 of the radially inner wall surface of the wall 36. The effect of this arrangement is that the tapered interfitting engagement between surfaces 15 and 38 provides an effective seal and any liquid which manages to find its way through this seal is retained in the volume indicated 59 in the drawing and is prevented from passing to the exterior because of the resilient engagement between the sealing and latching member 16 and the confronting portion of the wall 36. The angled surface 39 and the direction in which the sealing and latching member 16 extends cooperate to provide a resistance to separation of the two cooperating coupling elements. As can be seen, in order to separate the two elements, a force must be applied sufficient to bend over the tip portion 17 of the sealing and latching member 16.

The preferred cone angle for the interfitting engaging surfaces 15 and 38 is 10 degree cone angle, that is to say, a 5 degree angle to the central axis of rotation of the coupling element. However, any cone angle between about 4 degrees and about 16 degrees may be suitable, with a more preferred range being 6–10 degrees.

Figure 8:
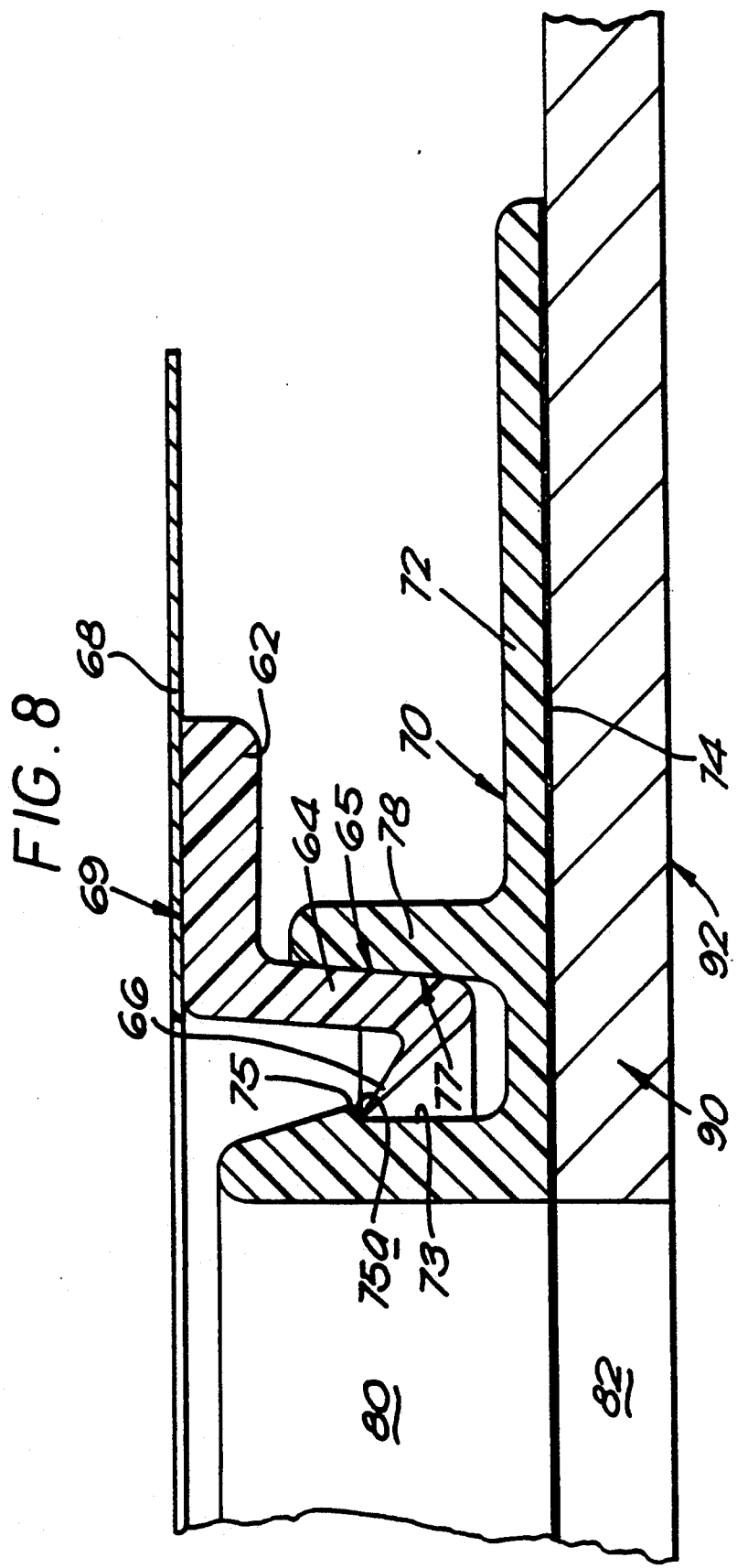
FIG. 8 is a cross-section in an axial plane, taken through the rotational axis of the coupling, showing half of a second embodiment of ostomy coupling according to the invention on a larger scale than used in FIGS. 9–12.
Figure 10:
Figure 12:
Figure 11:

A second embodiment of the invention will now be described with reference to FIGS. 8–12.

This embodiment of the invention illustrated is a two-part coupling by which an ostomy bag or pouch can be connected to a pad by using a light fitting pressure, but which requires a relatively heavier separating force to detach a filled bag with its bag-side coupling element from the body-side coupling element which remains on the medical grade adhesive pad.

This embodiment also adopts a two-stage approach to satisfactory sealing between the two coupling elements, involving the cooperation of substantially conically tapered surfaces on the body-side and bag-side coupling elements and the cooperation of a resilient plastic latching and sealing member on one element with a confronting projecting surface of special shape upon the other coupling elements.

The illustrated bag-side coupling element 60 comprises a substantially circular flange 62 having a flat surface 69 over which an ostomy bag wall 68 is secured by welding, adhesive or in any other convenient manner. Integral with the flange 62 is a first annular wall 64 which has a tapered outer wall surface 65 and, at its end further from the flange 62, has an integral sealing and latching member 66. This member 66 extends around the entire periphery of the bag-side coupling element 60. The element 60 is preferably made of a synthetic plastics material, for example ethylene vinyl acetate polymer. That known by the grade number UL00209 and available from Esso Petroleum Company Limited is an example of a suitable material. Of course other materials may be used.

A second (body-side) coupling element 70 includes a generally circular flange 72 surrounding a stomal orifice 80 and having a surface 74 which may be joined a pad 90 of a medical grade adhesive by, for example, an adhesive layer or by welding or in any other convenient way. The medical grade adhesive pad has a surface 92 which is intended for direct application to the peristomal area of the skin of the wearer. Suitable material for the pad 90 is that known as "Stomahesive" (Registered Trademark) or that known as "Duoderm" (Trademark) available from ConvaTec Limited, Ickenham Middlesex. Other suitable medical grade adhesive materials are available and may be employed instead. There is a stomal orifice 82 in the pad 40. Alternatively, the pad may carry a label marking the area of the centre of the pad which is to be cut out in order to produce a suitable stomal orifice. In use the intending wearer cuts out a central generally circular portion before application of the pad to the peristomal skin area. The second coupling element 72 may advantageously be made of low density polyethylene, e.g. Esso Grade 600 BA, but other suitable materials are available and may be used instead.

The second coupling element includes a radially inner annular wall 76 and a radially outer annular wall 78. The wall 78 has a substantially conically tapered inner surface 77. The taper of this surface is arranged to be complementary to that of the surface 65 of the coupling element 60. The height of the wall 76 is greater than the height of the wall 78. The shape of the radially inner wall surface of the wall 76 is not of any consequence except that it is desirable for it to be as smooth as possible so not offering any crevices or impediments to exit of discharged body wastes. In use, these pass from the stoma of the wearer into the bag, one wall 68 of which only is shown.

The inner annular wall 76 is of greater height than the wall 78 and its inner surface has a projection 75 which extends inwardly forming a "nose" at a precisely defined height. This projection 75 extends completely around the wall 76 and is bounded on its lower side as seen in the drawing by an angled annular surface 75a. The position of this projection and the position of the sealing and latching member 66 and the dimensions of the first and second coupling elements are chosen so that in the normal mutually coupled position of the two parts the tip of the sealing and latching member 66 takes up a position in contact with the angled join between the surface 75a and a lower part 73 of the radially inner wall surface of the wall 76. The effect of this arrangement is that the tapered interfitting engagement between surfaces 65 and 77 provides an effective seal and access of liquid to these sealing surfaces is largely prevented by the obstruction afforded by the sealing and latching member 66. The angled surface 75a and the direction in which the sealing and latching member 66 extends cooperate to provide a resistance to separation of the two cooperating coupling elements. As can be seen, in order to separate the two elements, a force must be applied sufficient to bend over the tip portion of the sealing and latching member 66.

The preferred cone angle for the interfitting engaging surfaces 65 and 77 is 10 degree cone angle, that is to say, a 5 degree angle to the central axis of rotation of the coupling element. However, any cone angle between about 4 degrees and about 16 degrees may be suitable, with a more preferred range being 6–10 degrees.

An advantage of the arrangement illustrated in FIGS. 8–12 is that any faecal matter deposited on or adhering to the radially outer surface of the wall 76 is cleared, when the coupling parts are separated, by the wiping action of the sealing and latching member 66 (which is resilient in nature).

I claim:

1. An ostomy coupling comprising first and second coupling elements capable of being coupled together;

said first coupling element including a planar first flange having a first annular wall projecting therefrom, said first annular wall having a free end with a sealing and latching member having a tapered portion angled toward the plane of said first flange, said tapered portion being tapered down to a deformable tip;

said second coupling element including a second flange having two concentric annular walls projecting therefrom, said annular walls being spaced apart to accommodate at least said tapered portion therebetween, said first annular wall having a first frusto-conically tapered wall surface, one of said two concentric annular walls having a second frusto-conically tapered wall surface complementary to said first frusto-conically tapered wall surface, the other annular wall including a projection having an angled annular surface facing said one annular wall, when said first and second coupling elements are coupled together said first and second frusto-conically tapered wall surfaces are contiguous and said angled annular surface provides resistance to removal of said tapered portion from between said annular walls, and provides resistance to the decoupling of said first and second coupling elements, said first and second coupling elements being decoupled upon said deformable tip being adequately bent over.

2. The ostomy appliance of claim 1 wherein one of said concentric annular walls has a height greater than said first annular wall.

3. The ostomy appliance of claim 1 wherein said annular wall having said projection has a lesser height than said first annular wall.

4. The ostomy appliance of claim 1 wherein during coupling of said first and second coupling members said latching member cooperates with said concentric annular walls to form a space capable of retaining a liquid.

5. The ostomy appliance of claim 2 wherein said first and second frusto-conically tapered wall surfaces have a cone angle of from 4° to 16°.

6. The ostomy appliance of claim 1 wherein one of said coupling elements includes a surface with medical grade adhesive for securing said coupling element to skin.

* * * * *